United States Patent
Nakayama

(10) Patent No.: US 10,433,795 B2
(45) Date of Patent: Oct. 8, 2019

(54) RADIATION IMAGING SYSTEM, IMAGE PROCESSING DEVICE, RADIATION IMAGING METHOD, AND IMAGE PROCESSING PROGRAM

(71) Applicant: FUJIFILM Corporation, Tokyo (JP)

(72) Inventor: Hiroki Nakayama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 758 days.

(21) Appl. No.: 14/865,859

(22) Filed: Sep. 25, 2015

(65) Prior Publication Data

US 2016/0089090 A1    Mar. 31, 2016

(30) Foreign Application Priority Data

Sep. 26, 2014    (JP) .................................. 2014-197317

(51) Int. Cl.
*A61B 5/00*    (2006.01)
*A61B 6/02*    (2006.01)
(Continued)

(52) U.S. Cl.
CPC .............. *A61B 6/025* (2013.01); *A61B 6/032* (2013.01); *A61B 6/0414* (2013.01); *A61B 6/12* (2013.01);
(Continued)

(58) Field of Classification Search
CPC ......... A61B 6/025; A61B 6/502; A61B 6/461; A61B 6/5205; A61B 6/032; A61B 6/0414; A61B 6/12; A61B 6/463; A61B 6/5223; A61B 6/5258; A61B 10/0233; A61B 2090/376
See application file for complete search history.

(56) References Cited

U.S. PATENT DOCUMENTS 5,967,982 A * 10/1999 Barnett .................. A61B 90/10
378/206
2009/0080765 A1* 3/2009 Bernard ................ G06T 11/006
382/154

FOREIGN PATENT DOCUMENTS

| JP | 2008-61858 A | 3/2008 |
| JP | 2012-245329 A | 12/2012 |
| JP | 2013-169360 A | 9/2013 |

* cited by examiner

*Primary Examiner* — Elmer M Chao
(74) *Attorney, Agent, or Firm* — Birch, Stewart, Kolasch & Birch, LLP

(57) ABSTRACT

Disclosed are a radiation imaging system, an image processing device, a radiation imaging method, and a non-transitory computer-readable recording medium having an image processing program recorded thereon which facilitate the confirmation of a positional relationship between an object of interest and a biopsy needle. In the system using a radiation imaging device as a mammography device, when performing a biopsy of a breast of a subject, the positional relationship is confirmed using a radiation image (projection image) obtained through tomosynthesis imaging. A control unit reconstructs the projection image to generate a tomographic image in a state where the needle is inserted into the breast and generates a reprojection image at a predetermined angle from the tomographic image. The control unit extracts an image of the needle from the projection image, synthesizes the extracted image of the needle into the projection image while aligning, and displays the projection image.

20 Claims, 8 Drawing Sheets

(51) Int. Cl.
- *A61B 6/00* (2006.01)
- *A61B 6/04* (2006.01)
- *A61B 6/12* (2006.01)
- *A61B 10/04* (2006.01)
- *A61B 10/02* (2006.01)
- *A61B 6/03* (2006.01)
- *A61B 90/00* (2016.01)

(52) U.S. Cl.
CPC .............. *A61B 6/461* (2013.01); *A61B 6/463* (2013.01); *A61B 6/502* (2013.01); *A61B 6/5205* (2013.01); *A61B 6/5223* (2013.01); *A61B 6/5258* (2013.01); *A61B 10/0233* (2013.01); *A61B 2090/376* (2016.02)

RADIATION IMAGING SYSTEM, IMAGE PROCESSING DEVICE, RADIATION IMAGING METHOD, AND IMAGE PROCESSING PROGRAM

CROSS-REFERENCE TO RELATED APPLICATIONS

The present application claims priority under 35 U.S.C. § 119 to Japanese Patent Application No. 2014-197317, filed on Sep. 26, 2014. Each of the above application(s) is hereby expressly incorporated by reference, in its entirety, into the present application.

BACKGROUND OF THE INVENTION

1. Field of the Invention

The present invention relates to a radiation imaging system, an image processing device, a radiation imaging method, and a non-transitory computer-readable recording medium having an image processing program recorded thereon.

2. Description of the Related Art

As a radiation imaging device which captures a radiation image, so-called mammography which captures a radiation image of a breast of a patient to be a subject is known. Furthermore, as an imaging method, tomosynthesis imaging in which radiation is exposed to a breast from a plurality of directions to capture a radiation image, and a tomographic image is generated based on the captured radiation image is known.

For the purpose of medical diagnosis, a biological examination (biopsy) in which a part of an object of interest of a patient is collected by a biopsy needle is generally performed. When performing a biopsy, in order to appropriately collect an object of interest, a radiation image is captured in a state where the biopsy needle is inserted into the patient, and the positional relationship between the object of interest and the biopsy needle is confirmed by the captured radiation image.

When performing a biopsy, as a technique for confirming the positional relationship between the object of interest and the biopsy needle by a computed tomography (CT) image or a radiation image, for example, the techniques described in JP2013-169360A, JP2012-245329A, and JP2008-61858A are known.

SUMMARY OF THE INVENTION

However, in the related art, it may be difficult to obtain an image in which both the biopsy needle and the object of interest have high visibility, and it may be difficult to confirm the positional relationship between the object of interest and the biopsy needle.

An object of the invention is to provide a radiation imaging system, an image processing device, a radiation imaging method, and a non-transitory computer-readable recording medium having an image processing program recorded thereon which facilitate the confirmation of the positional relationship between an object of interest and a biopsy needle.

In order to attain the above-described object, a radiation imaging system of the invention includes a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at each of different projection angles to capture a plurality of projection images by the radiation detector, a tomographic image generation unit which generates a plurality of tomographic images based on the plurality of captured projection images, a reprojection image generation unit which reprojects the plurality of tomographic images to generate a reprojection image corresponding to the projection image at a predetermined projection angle, and a synthesis unit which extracts an image representing the biopsy needle from one of the plurality of projection images and synthesizes the image representing the biopsy needle into the reprojection image.

In the radiation imaging system of the invention, the synthesis unit may extract the image representing the biopsy needle from a projection image corresponding to the predetermined projection angle among the plurality of projection images and may synthesize the image representing the biopsy needle into the reprojection image.

In the radiation imaging system of the invention, the synthesis unit may specify the position of the image representing the biopsy needle included in the reprojection image and may synthesize the extracted image representing the biopsy needle at the specified position.

In the radiation imaging system of the invention, the tomographic image generation unit may generate the plurality of images parallel to the imaging surface.

In the radiation imaging system of the invention, the synthesis unit may further perform enhancement processing for enhancing the image representing the biopsy needle to be synthesized.

The radiation imaging system of the invention may further include a display unit which displays a reprojection image with the image representing the biopsy needle synthesized by the synthesis unit.

In the radiation imaging system of the invention, the display unit may display the plurality of projection images, the radiation imaging system may further include a reception unit which receives the designation of at least one projection image from among the plurality of displayed projection images, and the synthesis unit may extract the image representing the biopsy needle from the designated projection image.

In the radiation imaging system of the invention, when the reception unit receives the designation of the projection image, the reprojection image generation unit may generate a reprojection image corresponding to the projection image with a projection angle corresponding to the designated projection image as the predetermined projection angle.

An image processing device of the invention which is used in the radiating imaging system includes the tomographic image generation unit which generates the plurality of tomographic images reconstructed based on projection images obtained by imaging the breast at different projection angles in a state where the biopsy needle collecting an object of interest is inserted into the breast, the reprojection image generation unit which reprojects the plurality of tomographic images generated by the tomographic image generation unit to generate the reprojection image corresponding to the projection image at the predetermined projection angle, and the synthesis unit which extracts the image representing the biopsy needle from one of the plurality of projection images, synthesizes the image representing the biopsy needle into the reprojection image generated by the reprojection image generation unit, and displays the reprojection image on the display unit.

A radiation imaging method of the invention includes, using the above-described radiation imaging system, acquiring the plurality of projection images from the radiation imaging device which includes the radiation detector configured to detect radiation and the imaging stand configured to include the radiation detector, and exposes the breast in the state where the breast placed on the imaging surface of the imaging stand and having the biopsy needle inserted into the breast to radiation at each of different projection angles to capture the plurality of projection images by the radiation detector, causing the tomographic image generation unit to generate the plurality of tomographic images based on the plurality of captured projection images, causing the reprojection image generation unit to reproject the plurality of tomographic images to generate the reprojection image corresponding to the projection image at the predetermined projection angle, and the synthesis unit which extracts the image representing the biopsy needle from one of the plurality of projection images and synthesizes the image into the reprojection image.

There is provided a non-transitory computer-readable recording medium having an image processing program of the invention recorded thereon, the image processing program causing a computer to execute processing for, using the radiation imaging system, acquiring the plurality of projection images from the radiation imaging device which includes the radiation detector configured to detect radiation and the imaging stand configured to include the radiation detector, and exposes the breast in the state where the breast placed on the imaging surface of the imaging stand and having the biopsy needle inserted into the breast to radiation at each of different projection angles to capture the plurality of projection images by the radiation detector, generating the plurality of tomographic images based on the plurality of captured projection images, reprojecting the plurality of tomographic images to generate the reprojection image corresponding to the projection image at the predetermined projection angle, and extracting the image representing the biopsy needle from one of the plurality of projection images and synthesizing the image into the reprojection image.

According to the invention, the effect of facilitating the confirmation of the positional relationship between the object of interest and the biopsy needle is obtained.

DESCRIPTION OF THE PREFERRED EMBODIMENTS

Figure 1:
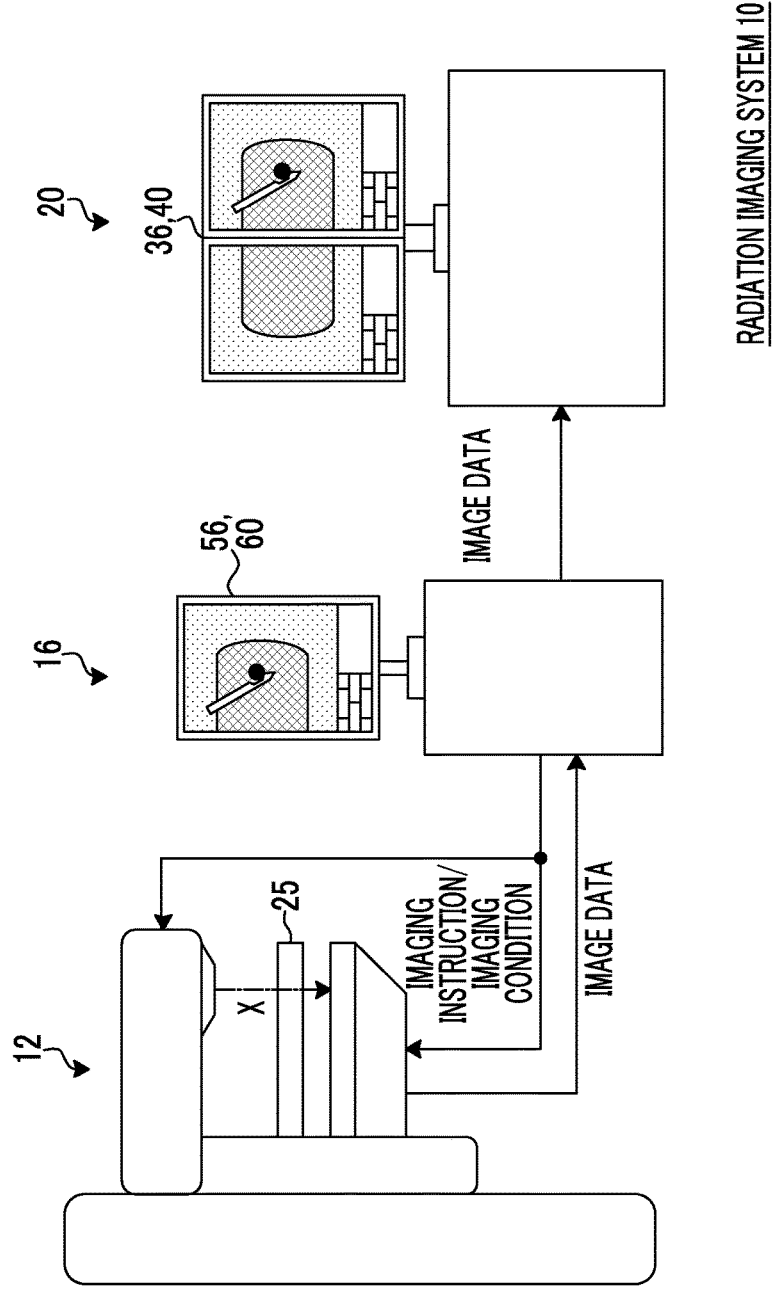
FIG. 1 is a schematic configuration diagram showing the outline of the overall configuration of an example of a radiation imaging system of a first embodiment.

Hereinafter, an embodiment of the invention will be described in detail referring to the drawings. This embodiment is not intended to limit the invention.

Figure 2:
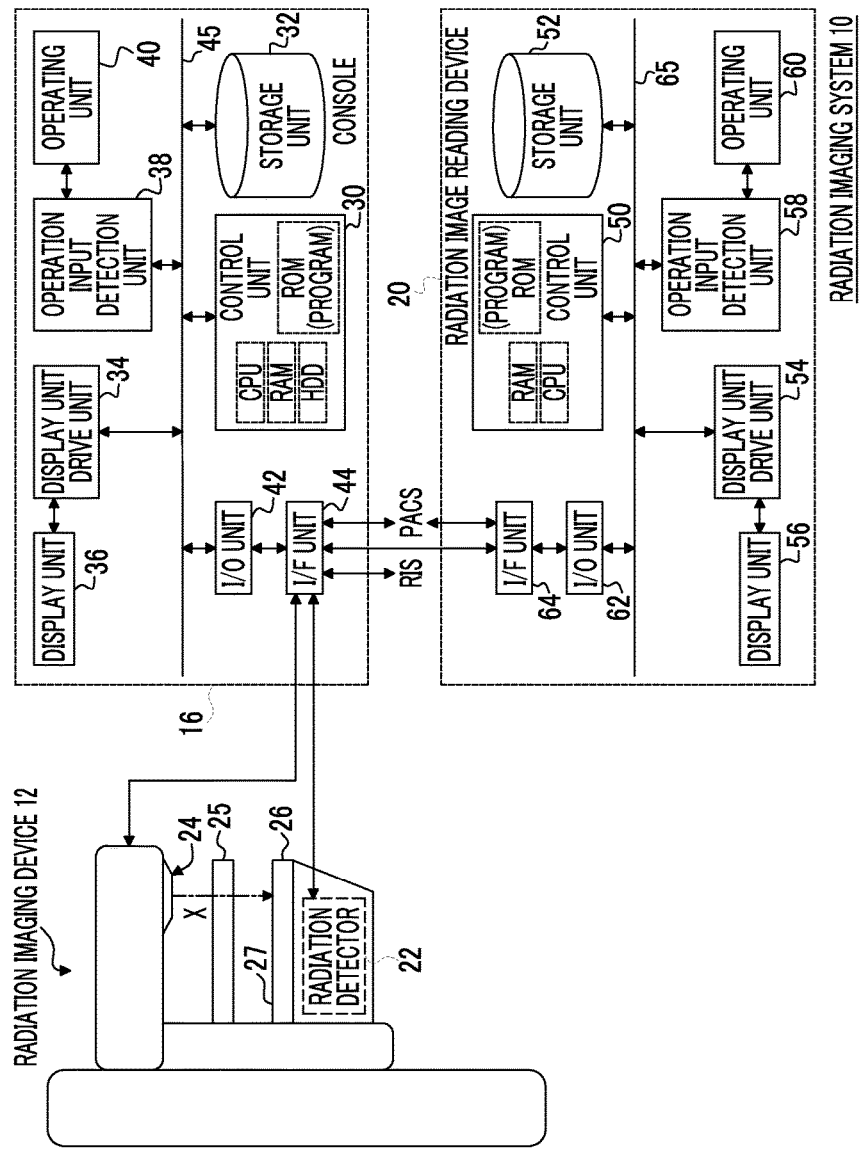
FIG. 2 is a schematic configuration diagram illustrating functions of an example of a console and a radiation image reading device in the radiation imaging system of the first embodiment.

First, the schematic configuration of the entire radiation imaging system of this embodiment will be described. FIG. 1 is a schematic configuration diagram of an example of the overall configuration of the radiation imaging system of this embodiment. FIG. 2 is a schematic configuration diagram illustrating functions of an example of a console 16 and a radiation image reading device 20 in the radiation imaging system of this embodiment.

The radiation imaging system 10 of this embodiment has a function of capturing a radiation image by an operation from a user, such as a physician or a radiology technician, based on an instruction (imaging menu) input from an external system (for example, a radiology information system (RIS)) through the console 16.

The radiation imaging system 10 of this embodiment includes a radiation imaging device 12, the console 16, and the radiation image reading device 20.

In the radiation imaging system 10 of this embodiment, a case where the console 16 generates and displays a tomographic image based on a radiation image captured through tomosynthesis imaging by the radiation imaging device 12 will be described. In this embodiment, a radiation image obtained through tomosynthesis imaging by a radiation detector 22 of the radiation imaging device 12 is referred to as a "projection image". A radiation image reconstructed based on the "projection image" is referred to as a "tomographic image". Furthermore, an image which includes the "projection image", the "tomographic image", and a "reprojection image" described below and is obtained using radiation or an image which is subjected to image processing is collectively referred to as a "radiation image".

The radiation imaging device 12 of the embodiment is a device which captures a radiation image of a breast of a subject, and is, for example, mammography. The radiation imaging device 12 may be a device which images the breast of the subject in a sitting state where the subject sits on a chair (including a wheelchair) or the like. The radiation imaging device 12 may be a device which is capable of individually imaging the right and left breasts of the subject in a state where at least the upper body of the subject is upright.

The radiation imaging device 12 has a radiation source 24, such as a tube lamp, which is provided to face an imaging surface 27 of an imaging stand 26, and exposes radiation X from the radiation source 24 toward the imaging surface 27.

When capturing the radiation image of the breast of the subject, one breast as an object is compressed with a compression plate 25 with respect to the imaging surface 27 of the imaging stand 26 and fixed, and radiation X is exposed from the radiation source 24 to the fixed breast. The compression plate 25 compresses the breast with respect to the imaging surface 27, and a member which transmits radiation is used as the compression plate.

Figure 3:
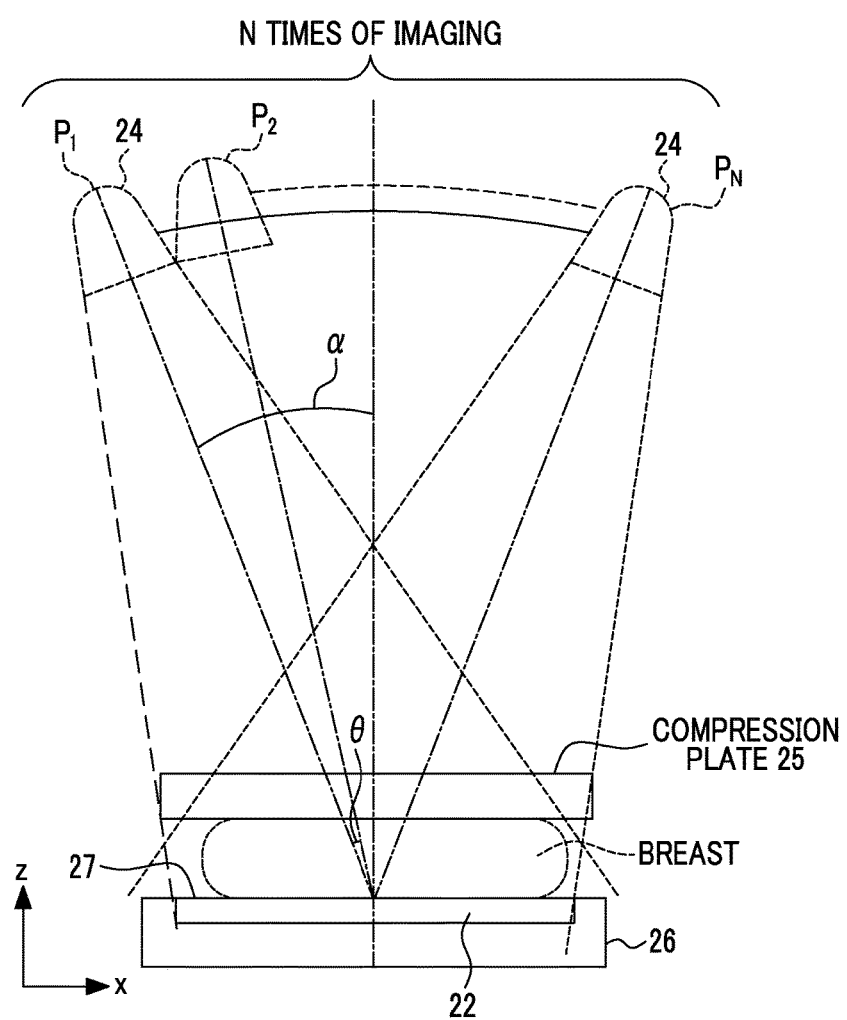
FIG. 3 is an explanatory view illustrating tomosynthesis imaging in the radiation imaging device of the first embodiment.

The radiation imaging device 12 of this embodiment is a device which is capable of performing imaging of at least a breast as an object at a plurality of projection angles (directions), so-called tomosynthesis imaging. FIG. 3 is an explanatory view illustrating tomosynthesis imaging in the radiation imaging device 12 of this embodiment. In the radiation imaging device 12, as shown in FIG. 3, when performing imaging (tomosynthesis imaging) of a breast at a plurality of projection angles, the radiation source 24 moves in an arc shape. In this embodiment, as shown in FIG. 3, imaging is performed at N places P1 to PN as the position of the radiation source 24 while moving an imaging position by a predetermined angle θ from an angle α.

The imaging stand 26 has the imaging surface 27. Inside the imaging stand 26, the radiation detector 22 to which radiation X transmitted through the breast as the object and the imaging surface 27 is exposed and which detects radiation X is arranged. Radiation X detected by the radiation detector 22 is visualized and a radiation image is generated. The radiation detector 22 receives exposure of radiation X with image data carried thereon, records image data representing a radiation image, outputs recorded image data, and detects an electric charge of each pixel generated according to the dose of exposed radiation X as image data. The radiation detector 22 of this embodiment is a flat panel detector (FPD), and is, for example, a direct conversion type panel using a Se layer where an electron is directly generated by exposed radiation. The radiation detector 22 is not limited to the direct conversion type panel, and an indirect conversion type panel or an electronic cassette may be used.

The radiation imaging device 12 of this embodiment is a device which is capable of collecting an object of interest, such as a tumor or calcification in the subject (breast), by a biopsy needle. Hereinafter, a case where an object of interest is collected using a needle as an example of a biopsy needle will be described. In this embodiment, a person, such as a physician, who performs observation, diagnosis, and the like of an object of interest, such as a tumor, by a captured radiation image is referred to as a "user", and a target to be observed, such as a tumor or calcification, of the user is referred to as an "object of interest". The collection of the object of interest is referred to as a "biopsy". In this embodiment, when performing a biopsy, tomosynthesis imaging is performed in a state where the needle is inserted into the object, and the user confirms the positional relationship between the object of interest and the needle (whether or not the needle is at an appropriate position for collecting the object of interest) from the obtained radiation image.

In this embodiment, image data representing a radiation image output from the radiation detector 22 of the radiation imaging device 12 is transmitted to the console 16. The console 16 of this embodiment has a function of controlling the radiation imaging device 12 using an imaging menu, various kinds of information, and the like acquired from an external system or the like through a wireless communication local area network (LAN) or the like. Furthermore, the console 16 of this embodiment has a function of transmitting and receiving various kinds of information to and from the radiation detector 22 of the radiation imaging device 12. Furthermore, the console 16 of this embodiment has a function of generating and displaying a tomographic image based on the radiation image acquired from the radiation detector 22. In addition, the console 16 of this embodiment has a function of transmitting the radiation image acquired from the radiation detector 22 or the generated tomographic image to the radiation image reading device 20.

The console 16 of this embodiment is an example of an image processing device, and is a server computer. As shown in FIG. 2, the console 16 includes a control unit 30, a storage unit 32, a display unit drive unit 34, a display unit 36, an operation input detection unit 38, an operating unit 40, an input/output (I/O) unit 42, and an interface (I/F) unit 44. The control unit 30, the storage unit 32, the display unit drive unit 34, the operation input detection unit 38, and the I/O unit 42 are connected so as to transmit and receive information and the like to and from one another through a bus 45, such as a system bus or a control bus.

The control unit 30 of this embodiment is an example of a tomographic image generation unit, a reprojection image generation unit, and a synthesis unit. The control unit 30 has a function of controlling the operation of the entire console 16. Furthermore, the control unit 30 has a function of performing the generation of a tomographic image, the generation of a reprojection image, and the like based on a projection image obtained through tomosynthesis imaging. The control unit 30 of this embodiment includes a central processing unit (CPU), a read only memory (ROM), a random access memory (RAM), and a hard disk drive (HDD). The CPU has a function of controlling the entire operation of the console 16. The ROM stores various programs and the like used in the CPU in advance. The RAM has a function of temporarily storing various kinds of data. The HDD has a function of storing and saving various kinds of data. The HDD may be a solid state drive (SDD) or may be used as the storage unit 32.

The display unit drive unit 34 has a function of controlling display of various kinds of information on the display unit 36. The display unit 36 of this embodiment has a function of displaying the imaging menu, image data, the radiation image, and the like. The operation input detection unit 38 has a function of detecting an operation state of the operating unit 40 or a processing operation on the operating unit 40. The operating unit 40 is used when the user issues an instruction relating to imaging of the radiation image, the generation of the tomographic image, and the like. The operating unit 40 may have a keyboard or a mouse as an example, or may be have a touch panel integrated with the display unit 36. Furthermore, the operating unit 40 may include a camera, and may have a function of inputting various instructions by making the camera recognize the gestures of the user.

The I/O unit 42 and the I/F unit 44 have a function of transmitting and receiving various kinds of information to and from an external system, such as the radiation imaging device 12 (the radiation source 24, the radiation detector 22, and the like), the radiation image reading device 20, or an RIS, and an external system, such as a picture archiving and communication system (PACS), by wireless communication or wired communication.

The storage unit 32 has a function of storing various kinds of data including image data, the radiation image, and the like received from the radiation detector 22.

The radiation image reading device 20 has a function of receiving image data, the radiation image, and the like from the console 16 and displaying the received image data, the radiation image, and the like. As a specific example of the radiation image reading device 20, a viewer or the like is given; however, the radiation image reading device 20 is not particularly limited, and a portable information terminal device which is a so-called personal digital assistance (PDA) represented by a tablet terminal, a smartphone, or the like may be used.

As shown in FIG. 2, the radiation image reading device 20 of this embodiment includes a control unit 50, a storage unit 52, a display unit drive unit 54, a display unit 56, an operation input detection unit 58, an operating unit 60, an I/O unit 62, and an I/F unit 64. The control unit 50, the storage unit 52, the display unit drive unit 54, the operation input detection unit 58, and the I/O unit 62 are connected so as to transmit and receive information and the like to and from one another through a bus 65, such as a system bus or a control bus.

The control unit 50 has a function of controlling the operation of the entire radiation image reading device 20. The control unit 50 includes a CPU, a ROM, and a RAM. The CPU has a function of controlling the operation of the entire radiation image reading device 20. The ROM stores various processing programs and the like used in the CPU in advance. The RAM has a function of temporarily storing various kinds of data.

The display unit drive unit 54 has a function of controlling display of various kinds of information including image data, the radiation image, and the like on the display unit 56. The operation input detection unit 58 has a function of detecting an operation state of the operating unit 60 or a processing operation on the operating unit 60. In this embodiment, the operating unit 60 is used when the user issues an instruction to the radiation image displayed on the display unit 56. In this embodiment, the operating unit 60 includes, for example, a touch panel, a touch pen, a plurality of keys, a mouse, and the like. When the operating unit 60 is constituted of a touch panel, the display unit 56 may have a touch panel and may include the function of the operating unit 60.

The I/O unit 62 and the I/F unit 64 have a function of performing communication of various kinds of communication with the console 16 or the PACS through wireless communication by electric waves, optical communication by light, or the like.

The storage unit 52 has a function of storing the radiation image received from the console 16. As a specific example of the storage unit 52, a nonvolatile memory or the like is given.

In this embodiment, various programs stored in the control unit 30 of the console 16 and the control unit 50 of the radiation image reading device 20 are stored in the ROMs of the control unit 30 and the control unit 50 in advance. However, the storage locations of various programs are not limited thereto, and various programs may be stored in a recording medium, such as a compact disk read only memory (CD-ROM) or a removable disk and may be installed from the recording medium on the ROM or the like. Furthermore, various programs may be installed from an external device on the ROM or the like through a communication line, such as the Internet.

Next, the action of the radiation imaging system 10 of this embodiment will be described referring to the drawings.

Figure 4:
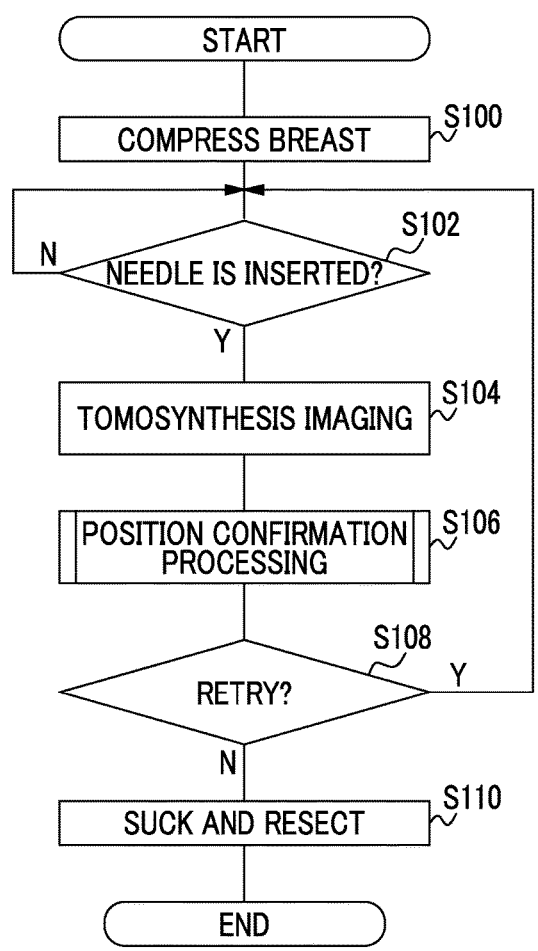
FIG. 4 is a flowchart showing an example of a biopsy in the radiation imaging system of the first embodiment.

FIG. 4 is a flowchart showing an example of the flow of a biopsy in the radiation imaging system 10 of this embodiment.

In the radiation imaging system 10, when capturing the radiation image, imaging is executed according to the imaging menu. When information for instructing a "biopsy" is included in the imaging menu, the control unit 30 of the console 16 determines to perform a biopsy and executes the biopsy according to the flowchart shown in FIG. 4.

In Step S100, the breast of the subject is compressed with the compression plate 25. The subject brings one breast to be an object into contact with the imaging surface 27 of the radiation imaging device 12. The control unit 30 of the console 16 instructs the radiation imaging device 12 to move the compression plate 25 toward the imaging surface 27. In the radiation imaging device 12, the breast is fixed by the compression plate 25.

Next, in Step S102, it is determined whether or not the needle is inserted. The insertion of the needle for collecting an object of interest in the breast is performed by the physician as the user. The needle is normally inserted at an angle and a direction intersecting a plurality of tomographic images obliquely with respect to the imaging surface 27.

When a biopsy unit (not shown) is provided in the radiation imaging device 12, the user may use the biopsy unit upon inserting the biopsy needle. If the needle is inserted to a collection position (specifically, a planned collection position) of the object of interest, a completion instruction to the effect of the completion of the insertion is performed by, for example, the operating unit 40. The control unit 30 of the console 16 is in a standby state that the completion instruction is issued, and if the completion instruction is issued, progresses to Step S104.

After the breast is compressed, the confirmation of positioning of the subject may be performed before the needle is inserted, that is, between Steps S100 and S102. In regard to the confirmation of positioning, for example, scout imaging where exposure of radiation X is performed such that the optical axis of radiation X is normal to the imaging surface 27 without rotating (moving) the radiation source 24, that is, at an angle of 0° may be performed to acquire a radiation image (scout image), and the user may confirm positioning. When the user determines that positioning is inappropriate by the scout image, the compression of the breast with the compression plate 25 may be released, the breast may be repositioned, and then, the process may return to Step S100 to repeat the processing.

If the insertion of the needle is completed, in Step S104, the control unit 30 of the console 16 instructs the radiation imaging device 12 to perform tomosynthesis imaging. When an imaging instruction to perform tomosynthesis imaging where imaging is performed on the breast from a plurality of directions is input, the radiation imaging device 12 of this embodiment performs imaging while moving the radiation source 24 in an arc shape without moving the imaging stand 26. Specifically, as shown in FIG. 3, exposure of radiation X based on respective imaging conditions is performed at N places of P1 to PN as the position of the radiation source 24 while moving the imaging position by the predetermined angle θ from the angle α. Radiation X individually exposed from the radiation source 24 is transmitted through the breast and then reaches the radiation detector 22.

If radiation X is exposed, the radiation detector 22 outputs image data representing the exposed radiation image (projection image) to the console 16. As described above, when exposure of radiation X is performed at N places of P1 to PN as the position of the radiation source 24, image data of N sheets of projection images is output to the console 16.

Figure 5:
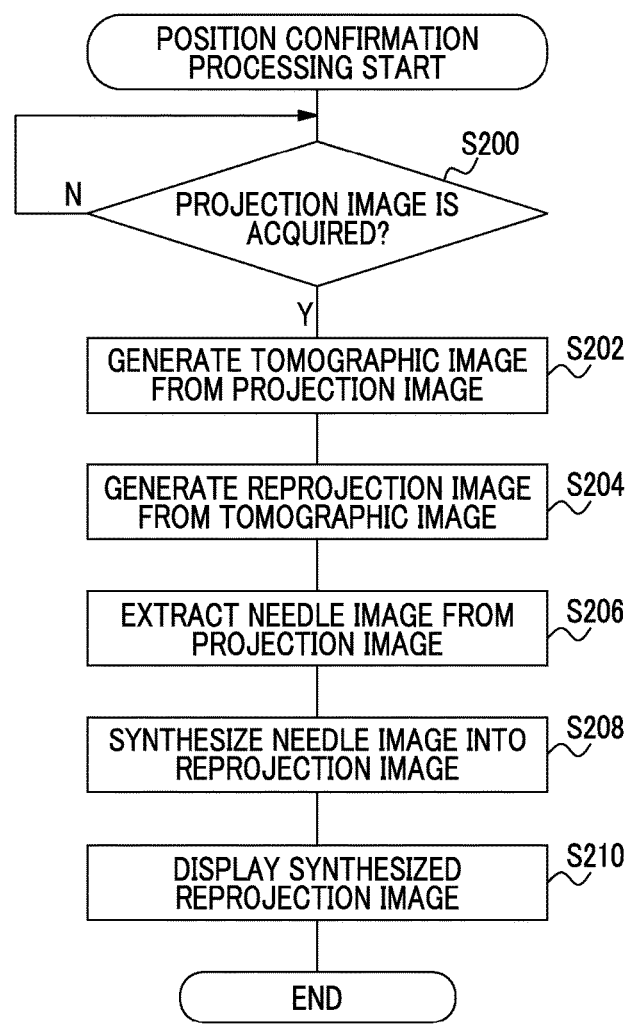
FIG. 5 is a flowchart showing an example of position confirmation processing which is executed by a control unit of the console of the first embodiment.
Figure 6:
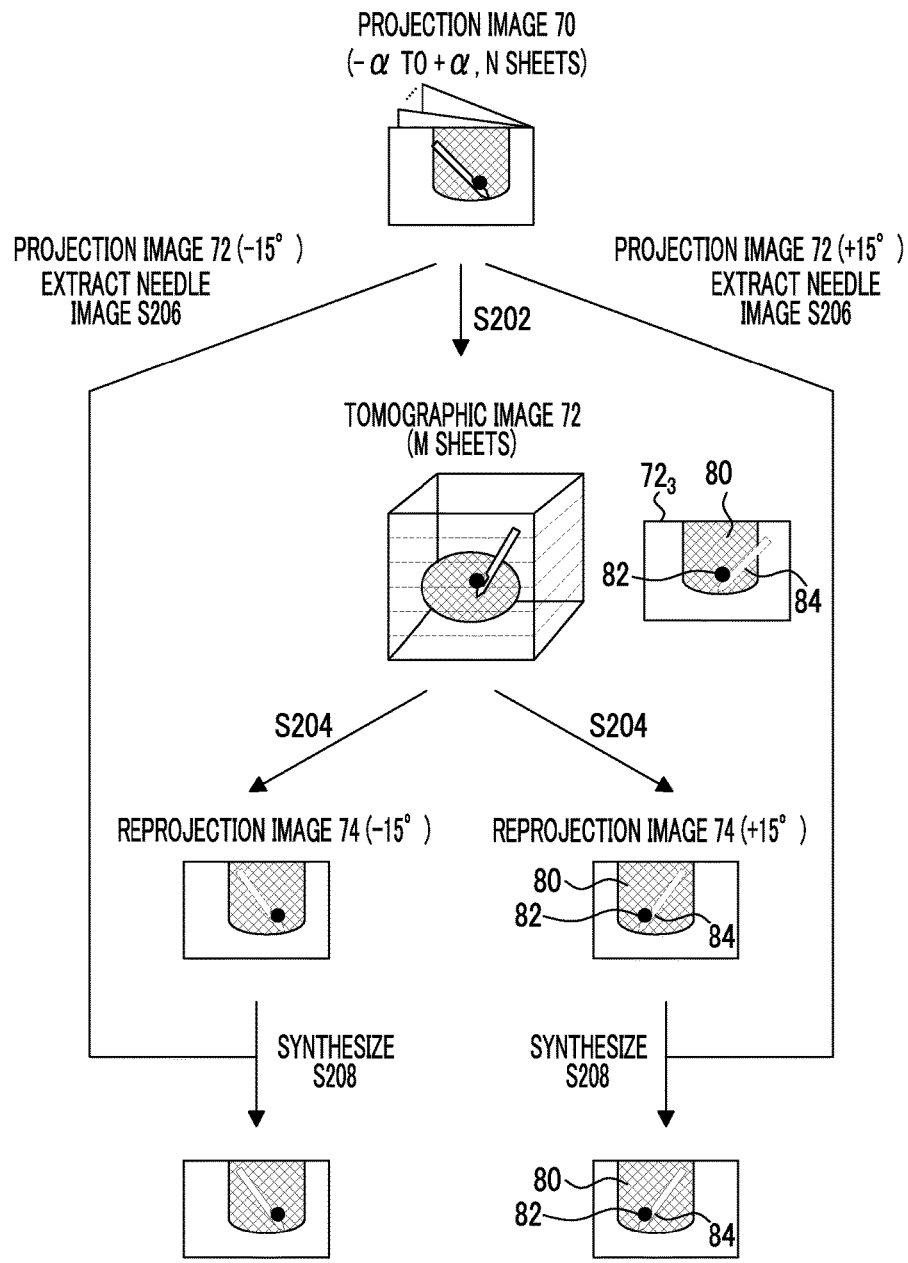
FIG. 6 is an explanatory view illustrating an example of the position confirmation processing of the first embodiment.

Next, in Step S106, the control unit 30 of the console 16 performs position confirmation processing for confirming the positional relationship between the object of interest and the needle. FIG. 5 is a flowchart showing an example of position confirmation processing which is executed by the control unit 30 of the console 16 of this embodiment. FIG. 6 is an explanatory view illustrating an example of position confirmation processing.

In Step S200, the control unit 30 of the console 16 determines whether or not N sheets of projection images (FIG. 6, projection images 70) are acquired. The control unit 30 of the console 16 can recognize the number of projection images 70 captured through tomosynthesis imaging from the imaging menu and the like. In this step, the control unit 30 determines whether or not all projection images 70 captured through tomosynthesis imaging are acquired from the radiation detector 22. When the projection images are not acquired, the standby state is placed, and when the projection images are acquired, the process progresses to Step S202.

In Step S202, the control unit 30 of the console 16 reconstructs a tomographic image (FIG. 6, a tomographic image 72) based on a plurality of acquired projection images 70 to generate a tomographic image 72 parallel to the imaging surface 27 at a predetermined slice thickness. In this embodiment, the term "parallel" includes "substantially parallel". FIG. 6 shows, as a specific example, a case where the control unit 30 generates M sheets of tomographic images 72.

The position where the object of interest is projected on the projection image 70 differs depending on the projection angle at which the radiation source 24 exposes radiation X. Accordingly, in the control unit 30, the amount of movement of the object of interest among a plurality of projection images 70 is calculated based on the projection angle at which the projection image 70 is captured, and the reconstruction of the tomographic image 72 is performed based on a known reconstruction method. The projection angle may be acquired from the imaging menu, or may be acquired from the radiation imaging device 12 (radiation detector 22) in association with each projection image 70.

The control unit 30 may display the generated tomographic image 72 on the display unit 36. At least a part of the M sheets of tomographic images 72 has an image 80 of the breast, an image 82 of the object of interest, and an image 84 of the needle like a third tomographic image 72$_3$ from the imaging surface shown in FIG. 6.

Figure 7:
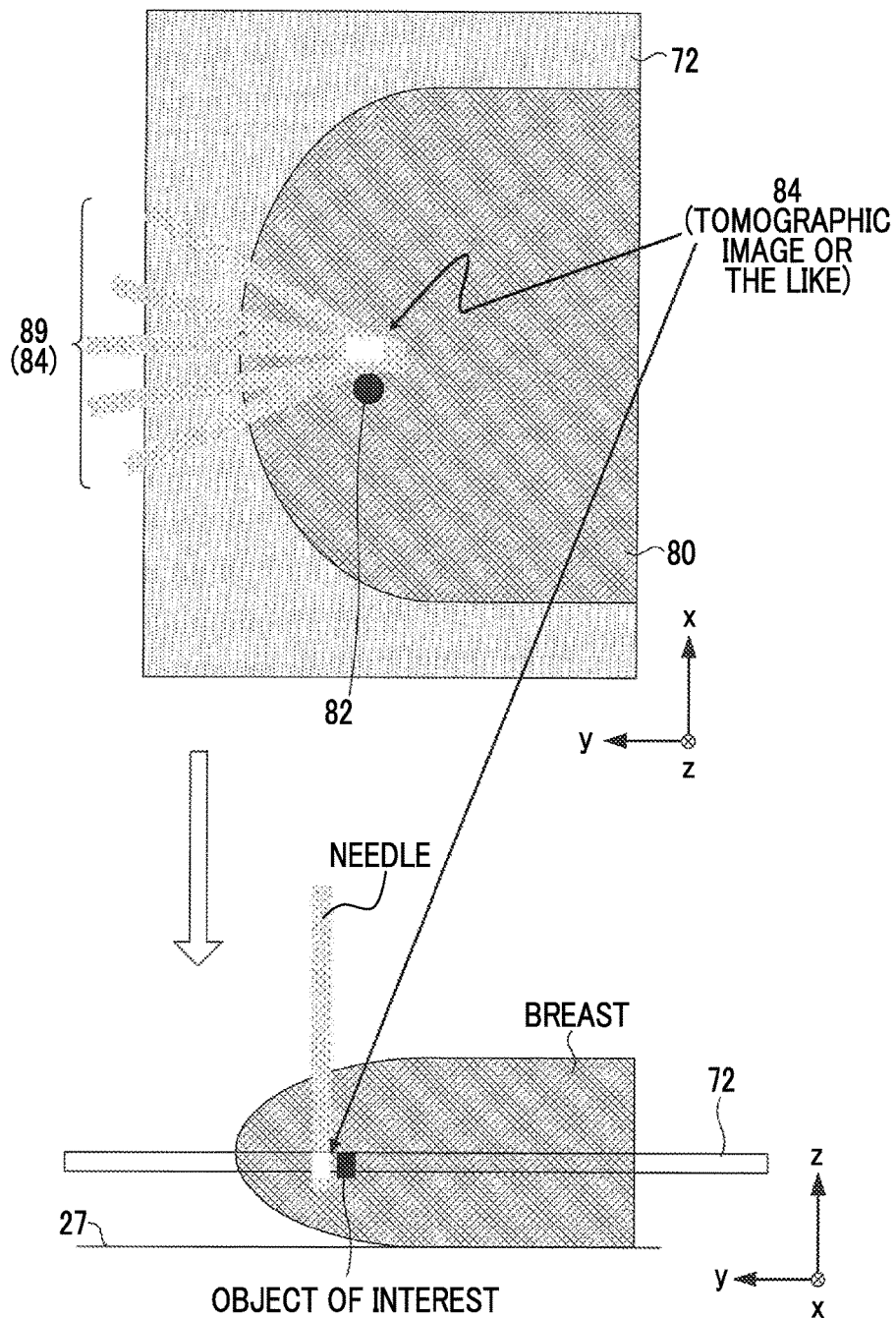
FIG. 7 is a schematic view of an example of a tomographic image in which an image of a breast, an image of an object of interest, and an image of a needle are imaged.

FIG. 7 is a schematic view of an example of the tomographic image 72 where the image 80 of the breast, the image 82 of the object of interest, and the image 84 of the needle are imaged. As described above, the tomographic image 72 is a radiation image reconstructed based on a plurality of projection images 70, and thus includes a great amount of information (amount of electric charge) compared to one sheet of projection image 70. Since the amount of information is great, in the tomographic image 72, the image 82 of the object of interest is easily viewed compared to one sheet of projection image 70. On the other hand, since the needle is inserted in a direction intersecting the tomographic image 72, in the image 84 of the needle, a portion of the image 84 of the needle corresponding to a tomographic plane (the height of the tomographic image 72) is brought into focus. For this reason, the image 84 of the needle is displayed clearly, specifically, as a white image. However, an image of the needle corresponding to a portion different from the tomographic plane (the height of the tomographic image 72) may be generated as an artifact 89, and visibility of the entire image 84 of the needle may be degraded. In this way, in the tomographic image 72, even if the image 82 of the object of interest can be visually recognized clearly, visibility of the image 84 of the needle is degraded, and it may be difficult to confirm the positional relationship between both of them, and in particular, the position of an opening of the needle for collecting an object of interest. Accordingly, in the radiation imaging system 10 (console 16) of this embodiment, a radiation image for facilitating the positional relationship between the object of interest and the needle is generated.

Next, in Step S204, the control unit 30 of the console 16 generates a reprojection image 74 from the tomographic image 72. The "reprojection image" is a pseudo two-dimensional radiation image which is reconstructed from the tomographic image, and corresponds to a projection image.

A method of reconstructing and generating the reprojection image 74 (pseudo two-dimensional image) from the tomographic image is not particularly limited, and for example, a technique described in US2010-0135558A may be used. In this embodiment, two sheets of reprojection images 74 according to two predetermined projection angles are generated. However, the number of reprojection images 74 to be generated is not particularly limited. Furthermore, a predetermined projection angle is not particularly limited. As a specific example, in general, ±15° which is an imaging angle used for imaging, such as the confirmation of positioning, is given.

Similarly to the tomographic image 72, since the reprojection image 74 includes information of a plurality of projection images 70, the image 82 of the object of interest may be easily viewed, while visibility of the image 84 of the needle may be degraded.

Next, in Step S206, the control unit 30 of the console 16 extracts the image 84 of the needle from the projection image 70. It is preferable that the projection image 70 from which the image 84 of the needle is extracted is the projection image 70 corresponding to a predetermined angle at which the reprojection image 74 is generated (that is, captured at a projection angle which is the same as or closest to the predetermined angle). In the specific example shown in this embodiment, the image 84 of the needle is extracted from the projection image 70 of each of ±15°.

A method of extracting the image 84 of the needle from the projection image 70 is not particularly limited. For example, the image 84 of the needle may be extracted by image analysis. Furthermore, when a biopsy unit is used, or the like, and when the approximate position, angle, or the like of the needle can be acquired, the control unit 30 may calculate the position of the image 84 of the needle in the projection image 70 based on the acquired position, angle, or the like of the needle and may extract the image 84 of the needle based on the calculated position. In this embodiment, the "extraction" of an image refers to cutting a specified image instead of simply specifying an image.

For the reason described above, in many cases, the image 84 of the needle in the projection image 70 has high visibility compared to the image 84 of the needle in the tomographic image 72 or the reprojection image 74.

Next, in Step S208, the control unit 30 of the console 16 synthesizes the extracted image 84 of the needle into the reprojection image 74 generated in Step S204. A synthesis method is not particularly limited. In this embodiment, the control unit 30 synthesizes the image 84 of the needle to be overlaid on the reprojection image 74. When synthesizing the image 84 of the needle, it is preferable to specify the position of the image 84 of the needle in the projection image 70 as an extraction source and to synthesize the image 84 of the needle at a position in the reprojection image 74 corresponding to the specified position.

In this way, the image 84 of the needle with high visibility extracted from the projection image 70 is synthesized into the reprojection image 74 having the image 82 of the object of interest with high visibility, whereby the positional relationship between the object of interest and the needle is easily confirmed.

Next, in Step S210, the control unit 30 of the console 16 displays the reprojection image 74 with the image 84 of the needle synthesized thereinto on the display unit 36 and then ends the position confirmation processing of Step S106.

If the position confirmation processing of Step S106 ends, the process progresses to Step 108. In Step S108, it is determined whether or not to retry the insertion of the needle. The user confirms the positional relationship between the object of interest and the needle by the reprojection image 74 displayed on the display unit 36 with the image 84 of the needle synthesized thereinto by the processing of Step S210 described above. When it is determined that the positional relationship is inappropriate, that is, there is a possibility that an object of interest cannot be appropriately collected, the user retries to insert the needle into the breast. In this embodiment, when retrying the insertion of the needle, the user instructs the effect with the operating unit 40. When an instruction to retry is received, the control unit 30 returns to Step S102 and repeats this processing. When retrying is not performed, the process progresses to Step S110.

In Step S110, after a tissue of the object of interest is sucked and resected by the needle, this processing ends.

Second Embodiment

In the first embodiment, a case where the image 84 of the needle extracted from the projection image 70 corresponding to a predetermined angle is synthesized into the reprojection image 74 at a predetermined angle (as a specific example, ±15°) determined in advance has been described. In this embodiment, a case where the image 84 of the needle is extracted from the projection image 70 designated by the user will be described.

In the first embodiment, the image 84 of the needle is extracted from the projection image 70 corresponding to a predetermined angle at which the image 84 of the needle is assumed to be visually recognized easily. However, in the projection image 70 at an angle other than the predetermined angle, the image 84 of the needle may be visually recognized easily, or the positional relationship of the object of interest may be understood easily. In the radiation imaging system 10 of this embodiment, a case where the image 84 of the needle (the projection image 70 from which the image 84 of the needle is extracted) is selectable by the user in this case will be described.

The configurations of the radiation imaging system 10, the radiation imaging device 12, the console 16, and the radiation image reading device 20 are the same as those in the first embodiment. The same configurations and operations as those in the first embodiment are represented by the same reference numerals, and detailed description thereof will not be repeated. In the radiation imaging system 10 of this embodiment, the I/O unit 42 and the I/F unit 44 of this console 16 function as an example of a reception unit which receives the designation of the projection image by the user.

In the radiation imaging system 10 of this embodiment, position confirmation processing which is executed by the control unit 30 of the console 16 in a biopsy is different from that in the first embodiment (see FIG. 4). For this reason, the position confirmation processing of this embodiment will be described in detail.

Figure 8:
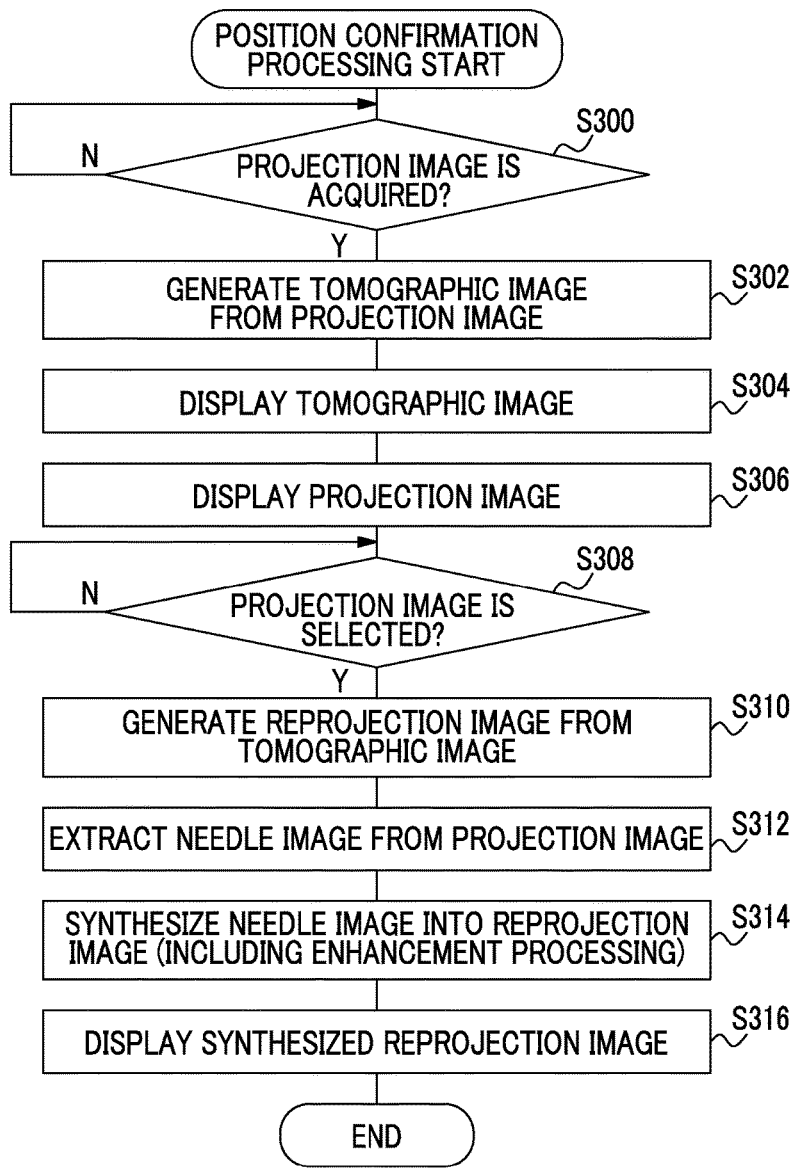
FIG. 8 is a flowchart showing an example of position confirmation processing which is executed by a control unit of a console of a second embodiment.

FIG. 8 is a flowchart showing an example of position confirmation processing which is executed by the control unit of the console of the second embodiment.

Similarly to Steps S200 and S202 of the position confirmation processing of the first embodiment, in Step S300 and S302, the control unit 30 of the console 16 determines whether or not N sheets of projection images 70 are acquired from the radiation imaging device 12 (radiation detector 22), and when the N sheets of projection images 70 are acquired, reconstructs the tomographic image 72 based on the projection images 70 to generate the tomographic image 72 parallel to the imaging surface 27 at a predetermined slice thickness.

Next, in Step S304, the control unit 30 of the console 16 displays the generated tomographic image 72 on the display unit 36. The user can confirm the object of interest by the displayed tomographic image 72. As described above, in the tomographic image 72, since the amount of information is great compared to the projection image 70, the image 82 of the object of interest is visually recognized easily.

Next, in Step S306, the control unit 30 of the console 16 displays the projection image 70 on the display unit 36. A way of displaying is not particularly limited. For example, all or a part of a plurality of acquired projection images 70 may be displayed in parallel on the display unit 36, or one projection image 70 may be displayed on the display unit 36 and the projection image 70 at a different projection angle may be sequentially switched according to a user's instruction.

The user confirms the projection image 70 displayed on the display unit 36 and selects at least one projection image 70, in which the image 84 of the needle is easily confirmed, by the operating unit 40. Alternatively, the projection image 70 or the like in which the positional relationship between the image 84 of the needle and the image 82 of the object of interest is easily understood is selected by the operating unit 40. The selected projection image 70 may be one, or two or more.

Next, in Step S308, it is determined whether or not the projection image 70 is selected by the user, and when the projection image 70 is selected, the process progresses to Step S310. That is, when the I/O unit 42 and the I/F unit 44 which function as an example of a reception unit receive the designation of the selected projection image 70, the process progresses to Step S310.

In Step S310, the reprojection image 74 is generated from the tomographic image 72. Although a generation method may be the same as Step S204 of the position confirmation processing of the first embodiment, in this embodiment, the reprojection image 74 is generated with a predetermined angle as a projection angle corresponding to the projection image 70 selected by the user.

Next, in Step S312, the image 84 of the needle is extracted from the projection image 70 selected by the user similarly to Step S206 of the position confirmation processing of the first embodiment.

Next, in Step S314, the image 84 of the needle extracted in Step S312 is synthesized into the reprojection image 74 generated in Step S310. A synthesis method of the image 84 of the needle may be the same as Step S208 of the position confirmation processing of the first embodiment, or synthesis may be performed after enhancement processing for enhancing the image 84 of the needle. The enhancement processing is not particularly limited, and for example processing for changing the color of the image 84 of the needle to a conspicuous color or for enhancing the color near the opening for collecting the object of interest is given. In this way, the processing for enhancing the image 84 of the needle may be performed in the position confirmation processing of the first embodiment.

Next, in Step S316, similarly to Step S210 of the position confirmation processing of the first embodiment, the reprojection image 74 with the image 84 of the needle synthesized thereinto is displayed on the display unit 36 and then this processing ends.

In this way, in the radiation imaging system 10 of this embodiment, the projection image 70 is selected from among a plurality of projection images 70, whereby the image 84 of the needle for use in confirming the positional relationship between the object of interest and the needle can be selected; therefore, the positional relationship between the object of interest and the needle is more easily confirmed. In the radiation imaging system 10 of this embodiment, the user can select the projection image 70 (the image 84 of the needle) while confirming the tomographic image 72 having the object of interest with high visibility displayed on the display unit 36; therefore, the projection image 70 (the image 84 of the needle) is easily selected.

As described above, in this embodiment, in the radiation imaging system 10 using the radiation imaging device 12 as a mammography device, when performing a biopsy of the breast of the subject, the positional relationship between the object of interest and the needle is confirmed using the radiation image (projection image 70) obtained through tomosynthesis imaging. The control unit 30 of the console 16 reconstructs the projection image 70 obtained through tomosynthesis imaging to generate the tomographic image 72 in a state where the needle is inserted into the breast, and generates the reprojection image 74 at a predetermined angle from the tomographic image 72. In addition, the control unit 30 of the console 16 extracts the image 84 of the needle from the projection image 70 at the predetermined angle, synthesizes the extracted image 84 of the needle into the reprojection image 74 while aligning, and displays the reprojection image 74 on the display unit 36.

In the tomographic image or the reprojection image, since the amount of information is great, the image of the object of interest is an image with high visibility. When performing tomosynthesis imaging, in particular, unlike CT, if the radiation imaging device is a mammography device, an imaging angle range is narrow; therefore, visibility of the image of the needle included in the tomographic image or the reprojection image may be degraded due to the needle being inserted in a direction intersecting the tomographic image. In particular, there is concern that visibility near the tip (the opening for collecting the object of interest) of the needle is degraded.

In a stereo image, the image of the needle has high visibility compared to the tomographic image or the reprojection image; however, since the amount of information becomes small, the image of the object of interest may be degraded.

When performing two times of imaging including imaging of the projection image for obtaining the tomographic image or the reprojection image having the image of the object of interest with high visibility and imaging of a stereo image having the image of the needle with high visibility, a burden imposed on the subject is increased.

In contrast, in the radiation imaging system 10 of this embodiment, a reprojection image having the image of the object of interest with high visibility and the image of the needle extracted from the projection image corresponding to the stereo image having the image of the needle with high visibility are synthesized through single tomosynthesis imaging. With this, in the radiation imaging system 10 of this embodiment, a reprojection image in which both of the image of the object of interest and the image of the needle (in particular, the opening) have high visibility can be obtained; therefore, the positional relationship between the object of interest and the needle is easily confirmed.

A reprojection image in which both of the image of the object of interest and the image of the needle (in particular, the opening) have high visibility can be obtained through single tomosynthesis imaging; therefore, it is possible to suppress a burden imposed on the subject.

In the respective embodiments described above, although the image 84 of the needle extracted from the projection image 70 is synthesized on the reprojection image 74, a synthesis method is not particularly limited as described above. For example, the image 84 of the needle in the reprojection image 74 may be deleted or the like, and the image 84 of the needle extracted from the projection image 70 may be replaced and synthesized.

In the respective embodiments described above, although the image 84 of the needle extracted from the projection image 70 is synthesized into the reprojection image, for example, the control unit 30 of the console 16 may synthesize a created image (illustration) of the needle or an image (an image by a photograph) of the needle stored in the console 16 in advance. When performing synthesis in this way, if the control unit 30 can recognize the state (position and angle, and the like) of the needle by the imaging menu, the biopsy unit (not shown), or the like, an image according to the state of the needle is preferably used.

In the respective embodiments described above, although a case where the control unit 30 of the console 16 has a function as a tomographic image generation unit which generates the tomographic image from the projection image 70, a function as a reprojection image generation unit which generates the reprojection image 74 from the tomographic image 72, and a function as a synthesis unit which extracts the image 84 of the needle from the projection image and synthesizes the image 84 of the needle into the reprojection image has been described, the invention is not limited thereto. For example, the control unit 50 of the radiation image reading device 20 may have the respective functional units. A part of the functional units may be provided in the control unit 30 of the console 16, and the other functional units may be provided in the control unit 50 of the radiation image reading device 20.

In the radiation imaging system 10 of the respective embodiments described above, although a case where the radiation imaging device 12 is a mammography device has been described, other radiation imaging devices may be provided. The object is not limited to the breast of the subject, and other regions may be provided, and are not particularly limited.

Radiation X which is used to capture the radiation image is not particularly limited, and X-rays, γ-rays, or the like can be applied.

In addition, the configurations and the operations of the radiation imaging system 10, the radiation imaging device 12, the console 16, and the radiation image reading device 20 described in this embodiment are an example, and may be changed according to the situation without departing from the gist of the invention. The flow of the biopsy or the flow of the position confirmation processing described in this embodiment is an example, and may be changed according to the situation without departing from the gist of the invention.

What is claimed is:

1. A radiation imaging system comprising:
   a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at each of different projection angles to capture a plurality of projection images by the radiation detector;

a processor configured to:
generate a plurality of tomographic images based on the plurality of captured projection images;
reproject the plurality of tomographic images to generate a reprojection image;
select one projection image from the plurality of captured projection images;
extract a portion image including an image of the biopsy needle, from the selected projection image; and
synthesize the portion image and the reprojection image by replacing or overlaying the portion image with an image of the biopsy needle in the reprojection image,
wherein the processor is further configured to calculate a position of the image of the needle in the selected projection image based on a position or angle of the needle, and extract the portion image based on the calculated position.

2. The radiation imaging system according to claim 1, wherein the processor is further configured to extract the image representing the biopsy needle from a projection image among the plurality of projection images and synthesizes the image representing the biopsy needle into the reprojection image.

3. The radiation imaging system according to claim 1, wherein the processor is further configured to specify the position of the image representing the biopsy needle included in the reprojection image and synthesizes the extracted image representing the biopsy needle at the specified position.

4. The radiation imaging system according to claim 2, wherein the processor is further configured to specify the position of the image representing the biopsy needle included in the reprojection image and synthesizes the extracted image representing the biopsy needle at the specified position.

5. The radiation imaging system according to claim 1, wherein the processor is further configured to generate the plurality of images parallel to the imaging surface.

6. The radiation imaging system according to claim 2, wherein the processor is further configured to generate the plurality of images parallel to the imaging surface.

7. The radiation imaging system according to claim 3, wherein the processor is further configured to generate the plurality of images parallel to the imaging surface.

8. The radiation imaging system according to claim 4, wherein the processor is further configured to generate the plurality of images parallel to the imaging surface.

9. The radiation imaging system according to claim 1, wherein the processor is further configured to perform enhancement processing for enhancing the image representing the biopsy needle to be synthesized.

10. The radiation imaging system according to claim 2, wherein the processor is further configured to perform enhancement processing for enhancing the image representing the biopsy needle to be synthesized.

11. The radiation imaging system according to claim 3, wherein the processor is further configured to perform enhancement processing for enhancing the image representing the biopsy needle to be synthesized.

12. The radiation imaging system according to claim 4, wherein the processor is further configured to perform enhancement processing for enhancing the image representing the biopsy needle to be synthesized.

13. The radiation imaging system according to claim 5, wherein the processor is further configured to perform enhancement processing for enhancing the image representing the biopsy needle to be synthesized.

14. The radiation imaging system according to claim 6, wherein the processor is further configured to perform enhancement processing for enhancing the image representing the biopsy needle to be synthesized.

15. The radiation imaging system according to claim 1, further comprising:
a display unit which displays a reprojection image with the image representing the biopsy needle synthesized by the processor.

16. The radiation imaging system according to claim 15, wherein the display unit displays the plurality of projection images,
the radiation imaging system further comprises:
a reception unit which receives the designation of at least one projection image from among the plurality of displayed projection images, and
the processor is further configured to extract the image representing the biopsy needle from the selected projection image.

17. The radiation imaging system according to claim 16, wherein, when the reception unit receives the selection of the projection image, the processor generates a reprojection image with a projection angle corresponding to the selected projection image.

18. A radiation imaging method comprising, using the radiation imaging system according to claim 1:
acquiring the plurality of projection images from the radiation imaging device which includes the radiation detector configured to detect radiation and the imaging stand configured to include the radiation detector, and exposes the breast in the state where the breast placed on the imaging surface of the imaging stand and the biopsy needle inserted into the breast to radiation at each of different projection angles to capture the plurality of projection images by the radiation detector;
causing the processor to generate the plurality of tomographic images based on the plurality of captured projection images;
causing the processor to reproject the plurality of tomographic images to generate the reprojection image;
causing the processor to select one projection image from the plurality of captured projection images;
causing the processor to extract a portion image including an image of the biopsy needle, from the selected projection image; and
causing the processor to synthesize the portion image and the reprojection image by replacing or overlaying the portion image with an image of the biopsy needle in the reprojection image,
wherein the processor is further configured to calculate a position of the image of the needle in the selected projection image based on a position or angle of the needle, and extract the portion image based on the calculated position.

19. A non-transitory computer-readable recording medium having an image processing program recorded thereon, the image processing program causing a computer to execute processing, the processing comprising:
acquiring a plurality of projection images from a radiation imaging device which includes a radiation detector configured to detect radiation and an imaging stand configured to include the radiation detector, and exposes a breast in the state where the breast placed on an imaging surface of the imaging stand and a biopsy needle inserted into the breast to radiation at each of different projection angles to capture a plurality of projection images by the radiation detector;

generating a plurality of tomographic images based on the plurality of captured projection images;
reprojecting the plurality of tomographic images to generate a reprojection image;
selecting one projection image from the plurality of captured projection images;
extracting a portion image including an image of the biopsy needle, from the selected projection image; and
synthesizing the portion image and the reprojection image by replacing or overlaying the portion image with an image of the biopsy needle in the reprojection image,
wherein the processor is further configured to calculate a position of the image of the needle in the selected projection image based on a position or angle of the needle, and extract the portion image based on the calculated position.

20. A radiation imaging system comprising:
a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at each of different projection angles to capture a plurality of projection images by the radiation detector;
a processor configured to:
generate a plurality of tomographic images based on the plurality of captured projection images;
reproject the plurality of tomographic images to generate a reprojection image having the same projection angle as one of the plurality of the projection images;
select one projection image from the plurality of captured projection images;
extract a portion image including an image of the biopsy needle, from the selected projection image; and
synthesize the portion image and the reprojection image by replacing or overlaying the portion image with an image of the biopsy needle in the reprojection image,
wherein the processor further configured to calculate a position of the image of the needle in the selected projection image based on a position or angle of the needle, and extract the portion image based on the calculated position,
wherein the selected projection image has the same projection angle as the reprojection image.

* * * * *